US010168261B2

(12) United States Patent
Oliver et al.

(10) Patent No.: US 10,168,261 B2
(45) Date of Patent: Jan. 1, 2019

(54) STRUCTURE FOR ACHIEVING DIMENSIONAL STABILITY DURING TEMPERATURE CHANGES

(71) Applicant: Nanomechanics, Inc., Oak Ridge, TN (US)

(72) Inventors: Warren Oliver, Knoxville, TN (US); Sudharshan Phani Pardhasaradhi, Knoxville, TN (US); Richard Anthony, Maryville, TN (US)

(73) Assignee: KLA-Tencor Corporation, Milpitas, CA (US)

(*) Notice: Subject to any disclaimer, the term of this patent is extended or adjusted under 35 U.S.C. 154(b) by 283 days.

(21) Appl. No.: 15/076,847

(22) Filed: Mar. 22, 2016

(65) Prior Publication Data

US 2016/0282243 A1    Sep. 29, 2016

Related U.S. Application Data

(60) Provisional application No. 62/136,930, filed on Mar. 23, 2015.

(51) Int. Cl.
*G01N 3/42* (2006.01)
*G01N 3/44* (2006.01)
(Continued)

(52) U.S. Cl.
CPC ............. *G01N 3/02* (2013.01); *G01B 5/0014* (2013.01); *G01N 3/42* (2013.01); *G01N 3/44* (2013.01); *G01N 3/46* (2013.01); *G01Q 30/10* (2013.01); *G01Q 70/04* (2013.01); *G02B 21/26* (2013.01); *H01J 37/20* (2013.01); *G01N 2203/0078* (2013.01); *G01N 2203/0222* (2013.01);
(Continued)

(58) Field of Classification Search
CPC ............ G01N 3/42–3/44; G01N 70/04; G01Q 30/10; G01Q 70/04; G01B 5/0014
See application file for complete search history.

(56) References Cited

U.S. PATENT DOCUMENTS 3,896,314 A    7/1975 Nuki et al.
4,703,181 A    10/1987 Swann et al.
(Continued)

FOREIGN PATENT DOCUMENTS

WO    2011066018    6/2011
WO    2013187972    12/2013

OTHER PUBLICATIONS

Extended European Search Report for European Patent App. No. 16769545.1, dated Oct. 15, 2018, 7 pages.

*Primary Examiner* — Paul M. West
(74) *Attorney, Agent, or Firm* — Luedeka Neely Group, P.C.

(57) ABSTRACT

A heated or cooled sample holding stage for use in a nanoindentation measurement system is described. The geometry of the design and the selection of materials minimizes movement of a sample holder with respect to a nanoindentation tip over a wide range of temperatures. The system controls and minimizes motion of the sample holder due to the heating or cooling of the tip holder and/or the sample holder in a high temperature nanoindentation system. This is achieved by a combination of geometry, material selection and multiple sources and sinks of heat. The system is designed to control both the steady state and the transient displacement response.

17 Claims, 5 Drawing Sheets

(51) Int. Cl.

| | | |
|---|---|---|
| *G01N 3/46* | (2006.01) | |
| *G01Q 30/10* | (2010.01) | |
| *G01Q 70/04* | (2010.01) | |
| *G02B 21/26* | (2006.01) | |
| *H01J 37/20* | (2006.01) | |
| *G01B 5/00* | (2006.01) | |
| *G01N 3/02* | (2006.01) | |

(52) U.S. Cl.
CPC ................ *G01N 2203/0286* (2013.01); *H01J 2237/2001* (2013.01); *H01J 2237/28* (2013.01)

(56) References Cited

U.S. PATENT DOCUMENTS

| | | | |
|---|---|---|---|
| 5,133,210 A | | 7/1992 | Lesko et al. |
| 5,173,605 A | * | 12/1992 | Hayes .................... B82Y 35/00 250/307 |
| 5,367,171 A | | 11/1994 | Aoyama et al. |
| 5,703,715 A | | 12/1997 | Gaul |
| 5,821,545 A | * | 10/1998 | Lindsay ................. G01Q 30/10 250/443.1 |
| 5,978,086 A | | 11/1999 | Aziz et al. |
| 7,315,412 B2 | | 1/2008 | Kinoshita et al. |
| 7,654,159 B2 | | 2/2010 | Enoksson et al. |
| 8,631,687 B2 | | 1/2014 | Patten et al. |
| 8,763,161 B2 | | 6/2014 | Cannara et al. |
| 2010/0212411 A1 | | 8/2010 | Passilly et al. |
| 2015/0028696 A1 | | 1/2015 | Oliver et al. |

\* cited by examiner

STRUCTURE FOR ACHIEVING DIMENSIONAL STABILITY DURING TEMPERATURE CHANGES

RELATED APPLICATIONS

This application claims priority to provisional U.S. patent application Ser. No. 62/136,930, filed Mar. 23, 2015, titled "Structure to Achieve Active Dimensional Stability During Temperature Changes."

FIELD

This invention relates to any field in which dimensional stability is required. This includes but is not limited to nanoindentation measurements. More particularly, this invention relates to compensating for dimensional changes due to temperature variations in such systems.

BACKGROUND

In applications involving various high-precision measurement instruments, such as scanning electron microscopes, precision optical systems, alignment systems and nanoindentation testing systems, maintaining the position of a sample holding stage with respect to a microscope focal point or the tip of a nanoindentation test probe is critical. Dynamic variations in temperature over time can cause undesirable movements of a sample platform with respect to a focal point or a measurement tip in a measurement system. Temperature variations can be particularly problematic in sample holding platforms that include heaters or coolers for making high or low temperature measurements.

What is needed, therefore, is a reliable system for heating or cooling the various components of the system while also compensating for movement of system components due to temperature variations.

SUMMARY

In various embodiments described herein, the above and other needs are met by a heated or cooled holding stage for holding a sample or a measurement tip or both for use in a nanoindentation measurement system. The geometry of the design and the selection of materials minimizes movement of the sample holder with respect to a nanoindentation tip over a wide range of temperatures. Preferred embodiments control and minimize motion of the sample and/or motion of the indentation tip due to the heating of the tip and/or the sample in a high temperature nanoindentation system. This is achieved by a combination of geometry, material selection and multiple sources and sinks of heat. Both the steady state and the transient displacement response can be controlled.

In embodiments described herein, a design goal is to minimize the net linear expansion or contraction of structural elements along a heat flow path that traverses one or more 180 degree changes in direction—in other words, a path that folds back on itself one or more times. The net linear expansion/contraction along the path depends on the lengths of the various components of the structure in the path, their thermal expansion coefficients, and the temperature gradient across each component. For purposes of modeling, one-dimensional heat flow is assumed, so that component lateral dimensions are not critical. The net linear expansion/contraction can be described as:

$$\text{net linear expansion/contraction} = L_i \alpha_i \Delta T_i$$

where, $L_i$, $\alpha_i$ and $\Delta T_i$ are the corresponding length along the direction of the path, the thermal expansion coefficient, and the temperature gradient across the component, respectively, for each component in the path. In the above equation, some values of $\Delta T_i$ are positive (in the +y direction) and some are negative (in the −y direction), depending on the direction of heat flow. As one skilled in the art will appreciate, the design goal is net zero expansion/contraction. From the above equation, it is apparent that there are multiple combinations of component lengths, component material properties, and component temperature gradients that can achieve a net zero expansion/contraction for steady-state or transient heat flow conditions. This equation also accounts for additional contributions to the expansion/contraction from radiation, especially at higher operating temperatures.

Some embodiments described herein provide a sample holding stage for a measurement instrument. The sample holding stage includes a sample holder, a support structure, and a housing. The sample holder includes a sample platform and a tubular support stem. The sample platform has an upper surface upon which a sample may be placed and a lower surface disposed below the upper surface. The tubular support stem has an upper portion that is rigidly affixed to the lower surface of the sample platform and a lower portion disposed below the upper portion. The support structure includes a base member, a tubular wall member, and a lip member. The base member is rigidly affixed to the lower portion of the tubular support stem. The tubular wall member has a lower portion that is rigidly affixed to the base member and an upper portion disposed above the lower portion. The lip member is rigidly affixed to the upper portion of the tubular wall member and has a central opening. The lip member is also rigidly affixed to the housing. The housing includes a central bore and an upper ledge that surrounds the bore. The central bore receives the base member and the tubular wall member of the support structure.

In preferred embodiments, at least a portion of the sample platform is disposed inside the central opening of the lip member, and the tubular support stem of the sample holder is disposed inside the tubular wall member of the support structure. When there is thermal expansion or contraction, the sample platform can move axially with respect to the tubular wall member, and the base member of the support structure can move axially with respect to the housing.

In some embodiments, the sample platform, the tubular wall member, the central opening of the lip member, and the central bore of the housing are all cylindrical. The inner diameter of the tubular wall member is greater than the sample platform diameter, so that the sample platform can move axially with respect to the tubular wall member. The inner diameter of the central opening of the lip member is greater than the sample platform diameter, so that the sample platform can move axially with respect to the central opening of the lip member. The diameter of the central bore of the housing is greater than the outer diameter of the tubular wall member, so that the tubular wall member can move axially with respect to the central bore of the housing.

In some embodiments, the sample holder is formed of molybdenum, the support structure is formed of stainless steel, and the housing is formed of copper.

In some embodiments, a heat transfer element is disposed within the sample platform for transferring heat into or removing heat from the sample platform.

In another aspect, embodiments described herein provide an indentation tip holding stage for a measurement instrument. The indentation tip holding stage includes a housing, a support structure, and a tip holder. The housing has an outer surface and a central bore extending into the housing from its outer surface. The support structure includes a central portion disposed at least partially inside the central bore of the housing. A central bore in the support structure, which extends into the central portion, has a bore opening in an outer surface of the central portion and a bore end spaced apart from the bore opening. A lip member, which extends outwardly from the central portion, is rigidly affixed to the outer surface of the housing. The tip holder, which is disposed at least partially inside the central bore of the support structure, includes a receiving portion and an attachment portion. The receiving portion, which is disposed adjacent the bore opening in the central portion, receives and holds an indentation tip. The attachment portion, which is disposed inside the central bore of the support structure, is rigidly affixed to the central portion of the support structure adjacent the bore end. When there is thermal expansion or contraction, the central portion of the support structure can move axially within the central bore in the housing, and the receiving portion of the tip holder can move axially within the central bore of the support structure.

In some embodiments, the tip holder is formed of molybdenum, the support structure is formed of stainless steel, and the housing is formed of copper.

In some embodiments, a heat transfer element is disposed within the central portion of the support structure for transferring heat into or removing heat from the tip holder.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION

As the terms are used herein, "upper," "lower," "above," and "below" indicate spatial positions or relationships of various components of the structure with reference to the y-axis (vertical axis) of an x-y-z coordinate system. Thermal expansion and contraction, and compensation therefor, are also described as occurring along component axes that are disposed in the y-direction. It will be appreciated that the structures described herein could be rotated such that the component axes are disposed in the x-direction or z-direction (or any other direction), in which case the terms above that describe spatial positions or relationships are transformed to the relevant component axes. Thus, the invention is not limited to a vertical orientation, nor is it limited to any other particular orientation of the structure with respect to any particular axis of a coordinate system.

Figure 1:
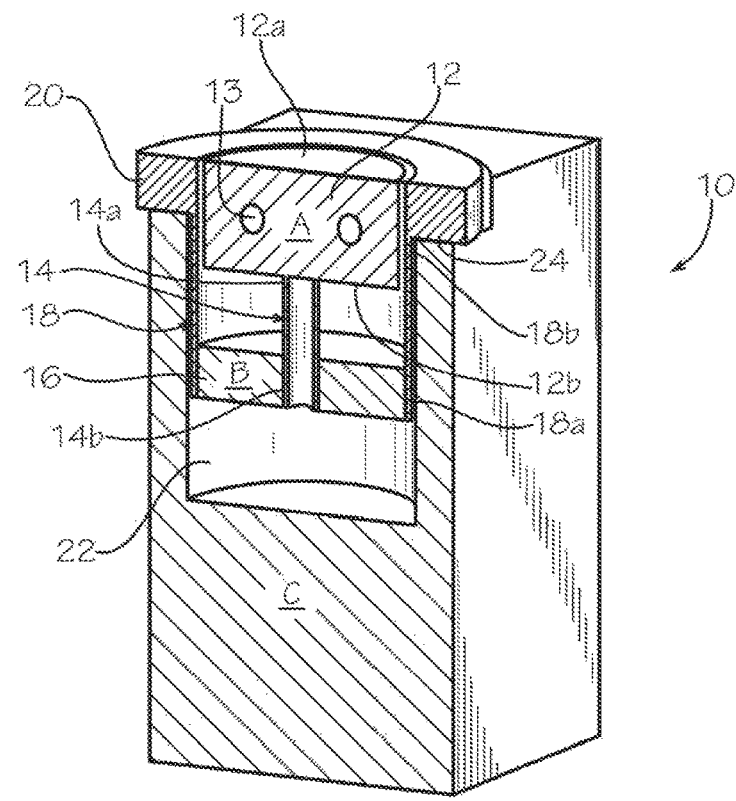
FIGS. 1-3 depict a sample holding stage according to an embodiment of the invention.
Figure 2:
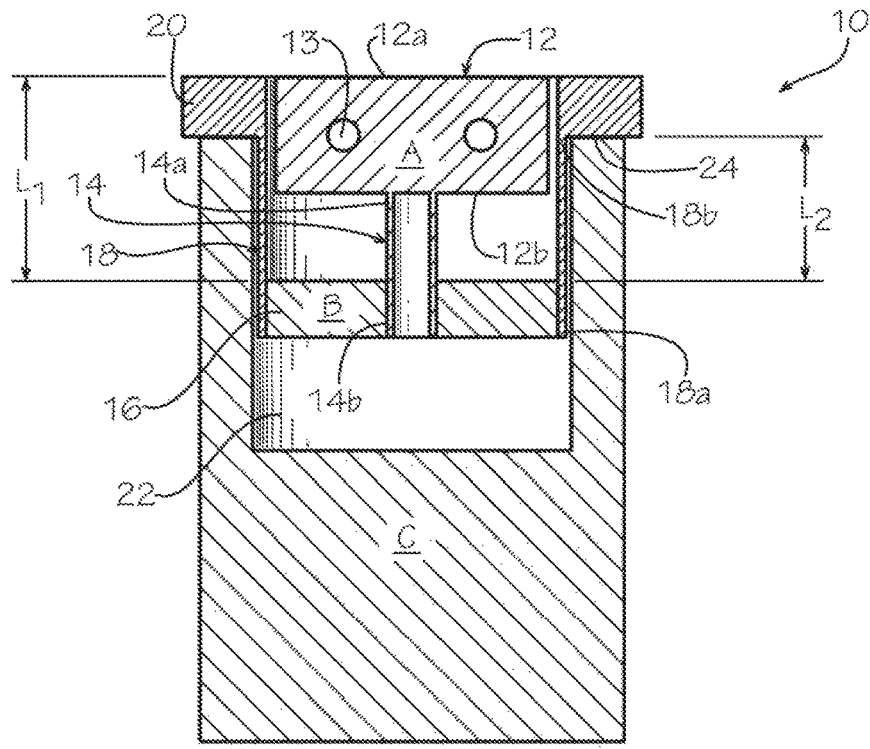
Figure 3:
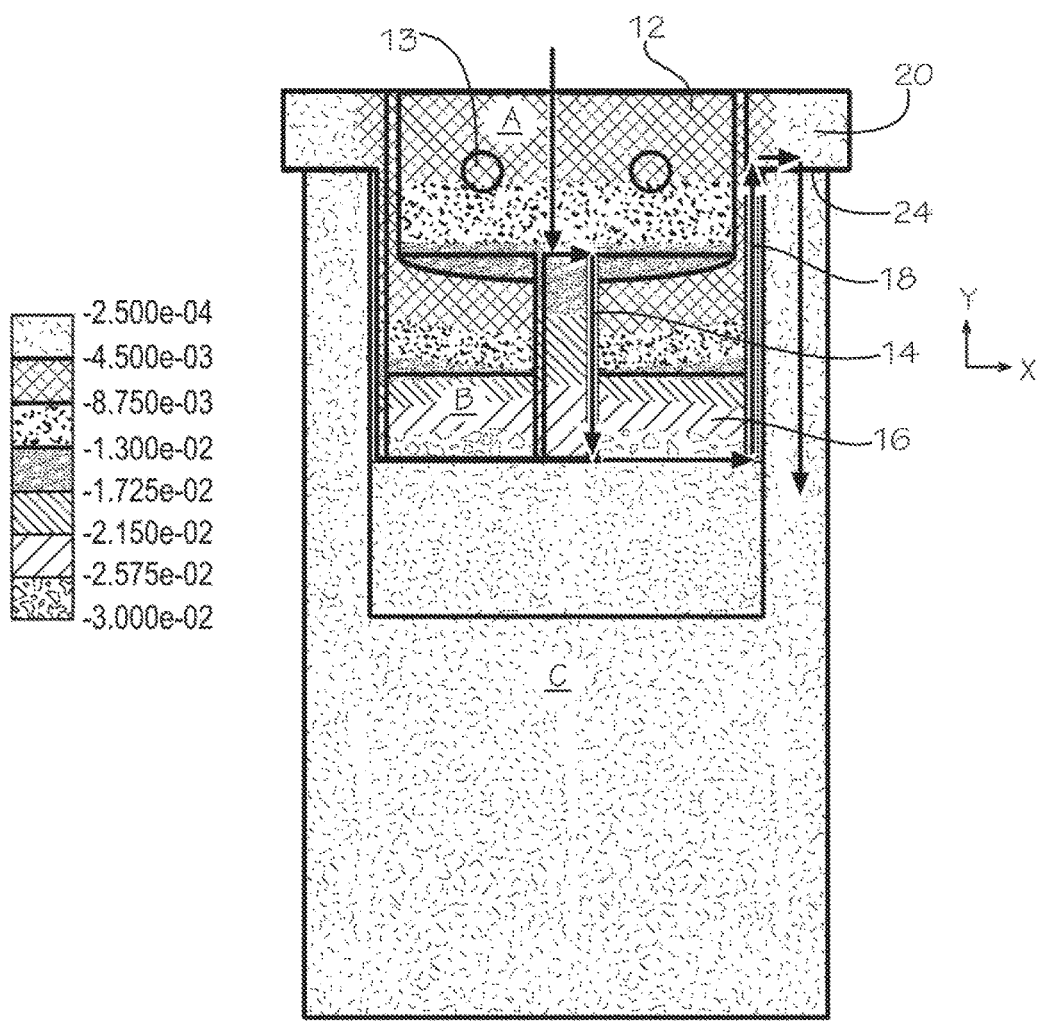

FIGS. 1, 2 and 3 depict a cutaway view of a preferred embodiment of a sample holding stage 10, comprising a sample holder A, a support structure B and a housing C. The sample holder A, which may be heated or cooled, includes a sample platform 12 and a support stem 14.

The sample platform 12 and the support stem 14 are both preferably formed from molybdenum, which has a coefficient of thermal expansion of $2.8 \times 10^{-6}$ in/(in R). The sample platform has an upper surface 12a for receiving a sample and a lower surface 12b for engaging the support stem 14. In a most preferred embodiment, the sample platform 12 is cylindrical. Generally, the diameter of the sample platform 12 depends on the size of sample to be accommodated. From a heat compensation standpoint, the diameter of the platform is generally not critical, as only axial displacements are of interest. However, it will be appreciated that the outer diameter of the platform must be less than the inner diameter of the lip 20 of the support structure, so that the platform 12 can move freely in the axial direction with respect to the lip 20 as the structures expand and contract with changes in temperature. In one embodiment, the diameter of the sample platform is 12.5 mm.

A heat transfer element 13 may be disposed within the platform 12. In some embodiments, the heat transfer element 13 is an electric heater element for providing heat to a sample material disposed on the platform. In some embodiments, the heat transfer element 13 is a heat sink for cooling the sample. The thickness (axial height) of the platform 12 is preferably determined by the minimum space required to accommodate the heat transfer element 13.

The support stem 14 includes an upper portion 14a and a lower portion 14b. In a most preferred embodiment, the support stem 14 is cylindrical. However, it should be appreciated that the support stem 14 could have any other tubular shape. Because one purpose of the support stem 14 is to throttle heat flow, its axial height (y direction) is as small as possible while still accommodating structures at either end that may be needed to attach the stem 14 to adjacent components. In one embodiment, the total axial height of the support stem is 7.8 mm. The thickness of the tubular wall of the stem 14 is preferably as small as possible while still providing sufficient mechanical strength. In a preferred embodiment, the upper portion 14a of the stem 14 is attached to the lower surface 12b of the platform 12 by high-temperature brazing.

The support structure B comprises a base portion 16, a tubular wall member 18 and an upper lip member 20, which are all preferably formed from stainless steel (such as type 304) having a coefficient of thermal expansion of $9.6 \times 10^{-6}$ in/(in R).

Figure 6B:
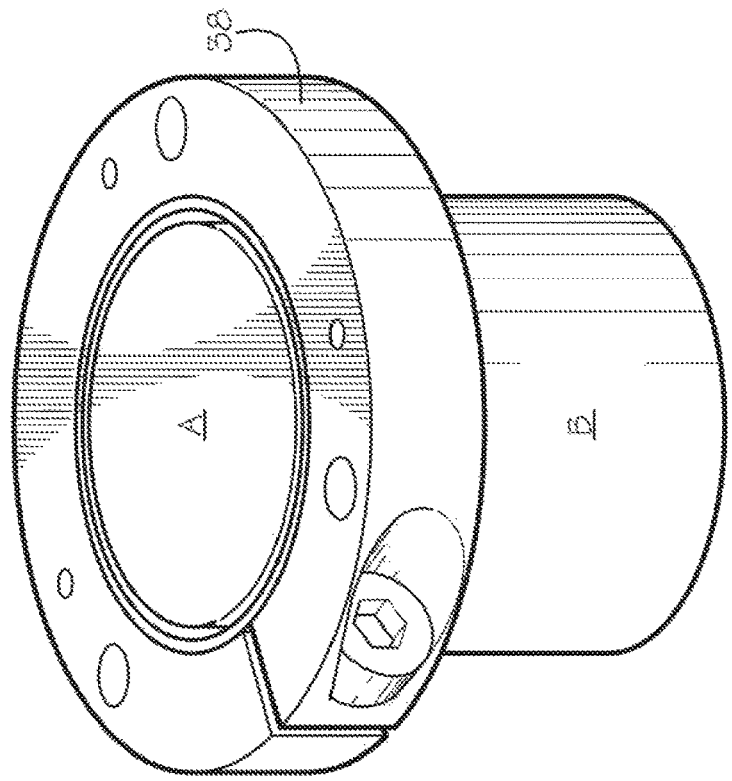
FIGS. 6A and 6B depict a sample holding stage according to an alternative embodiment.
Figure 6A:
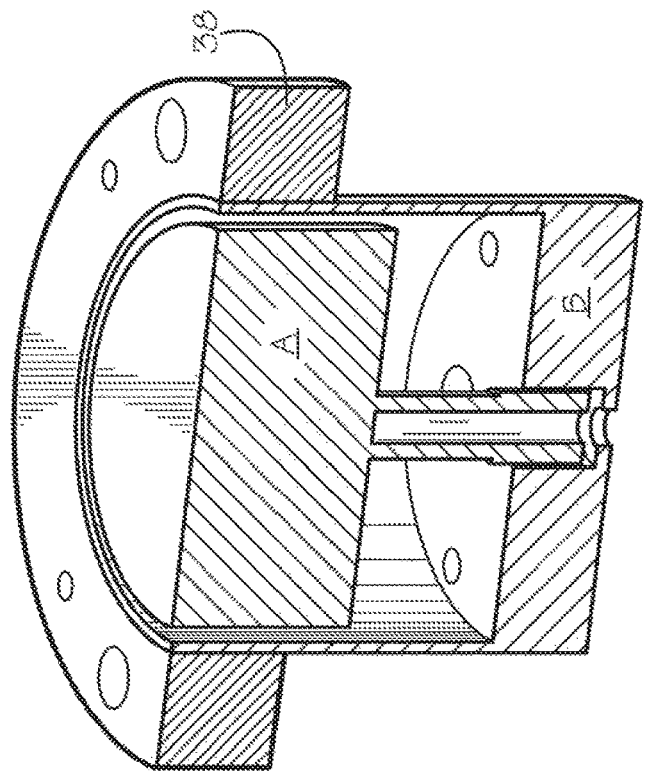

The tubular wall member 18 has a lower wall portion 18a and an upper wall portion 18b. In a most preferred embodiment, the tubular wall member 18 is cylindrical. However, it should be appreciated that the tubular wall member 18 could have any other tubular shape. The axial height (y direction) of the tubular wall member 18 depends on the choice of materials and lengths of other components in the heat flow path. In one embodiment, the axial height of the tubular wall member is 11.7 mm. The effective height of the tubular wall member 18 can be adjusted by replacing the upper lip member 20 with a similar-sized circular clamp 38 that can slide onto the tubular wall member 18, such as shown in FIGS. 6A and 6B. The wall thickness of the tubular wall member 18 is preferably as small as possible to throttle heat flow, while not compromising needed mechanical strength. In one embodiment, the wall thickness of the tubular wall member is 0.38 mm. From a heat compensation standpoint, the diameter of the tubular wall member 18 is generally not critical, as only axial displacements are of interest. In one embodiment, the outer diameter of the tubular wall member is 14.5 mm. It will be appreciated that the inner diameter of the tubular wall member 18 must be greater than the outer diameter of the platform 12, so that the platform 12 can move freely in the axial direction with respect to the tubular wall member 18 as the structures expand and contract with changes in temperature. The upper lip member 20 and the upper wall portion 18b can be made as one continuous piece, such as by machining the structure from a single piece of stainless steel. Alternatively, the upper lip member 20 may be shrink fit onto the upper wall portion 18b. In one embodiment, the outer diameter of the upper lip member member is 22 mm.

The thickness (axial height) of the base portion 16 is preferably as small as possible while still permitting the fastening of the base portion to the lower portion 14b of the stem 14, and preventing excessive distortion of the lower wall portion 18a to which the base portion 16 is fastened. In one embodiment, the axial height of the base portion is 3.5 mm. The lower portion of the stem 14b can be attached to the base portion 16 in various ways, such as by welding, fastening by a set screw, shrink fit, or a combination of these. The base portion 16 and the lower wall portion 18a can be made as one continuous piece, such as by machining the structure from a single piece of stainless steel. Alternatively, the base portion 16 may be shrink fit into the lower wall portion 18a.

The housing C, which is preferably formed from copper (coefficient of thermal expansion=9.3×10$^{-6}$ in/(in R)), has a central bore 22 and an upper ledge portion 24. In a most preferred embodiment, the central bore 22 is cylindrical. However, it should be appreciated that the central bore 22 could have any other tubular shape. The upper lip member 20 of the support structure B is fixedly attached to the upper ledge portion 24 of the housing C, such as with threaded bolts.

As depicted by the arrows in FIG. 3, heat generated by a heat transfer element 13 in the sample platform 12 flows through the walls of the support stem 14, through the base portion 16, tubular wall member 18, and upper lip member 20 of the support structure B, and finally into the copper housing C. Because the support stem 14 of the sample holder is fixed to the base portion 16 of the support structure, the upper surface 12a of the platform 12 moves in the +Y direction due to thermal expansion of the platform 12 and stem 14. Because the lip 20 of the support structure B is fixed to the ledge 24 of the housing C, which is maintained at a constant lower temperature, the base portion 16 of the support structure B moves in the −Y direction due to thermal expansion of the support structure.

Figure 4:
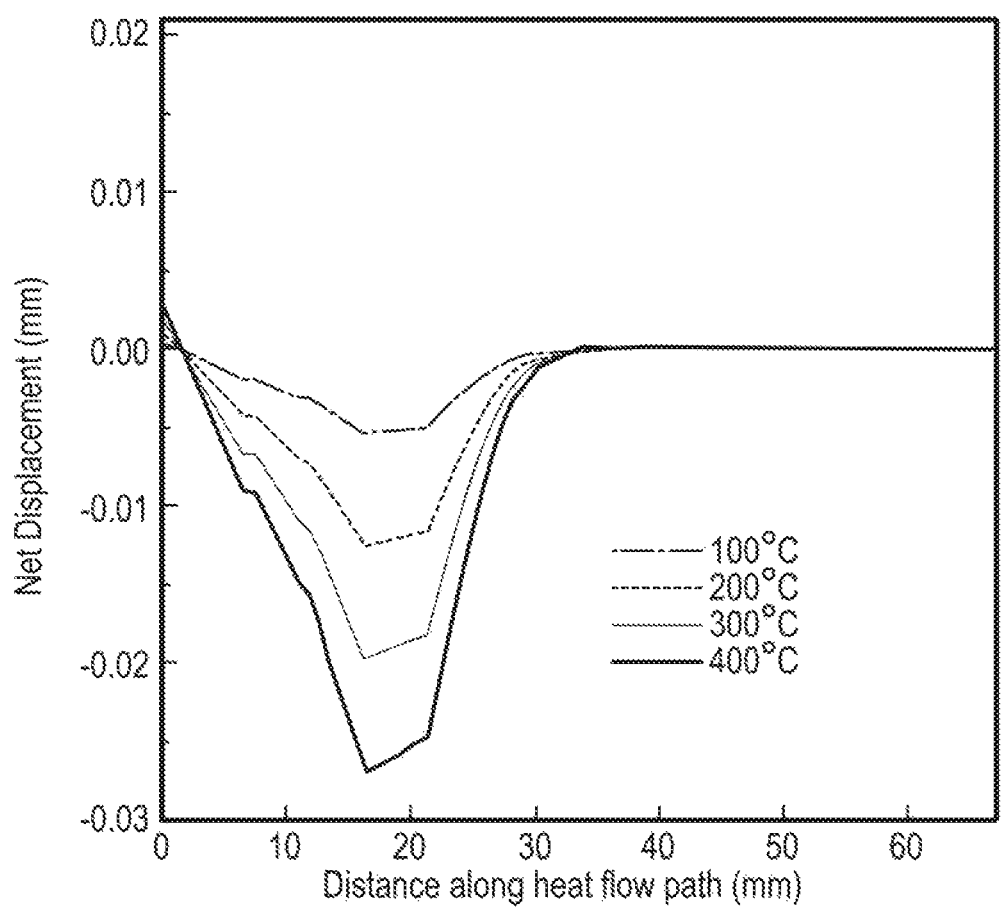
FIG. 4 depicts a plot of displacement versus distance along a heat flow path in the sample holding stage depicted in FIGS. 1-3.

The offsetting +Y and −Y movements of the structure result in the upper surface 12a of the platform 12 maintaining an essentially constant position as the structure heats up or cools down. This offsetting effect is illustrated in FIG. 4, which is a plot of net displacement versus distance along the heat flow path over a temperature range of 100° C. to 400° C.

With reference to FIG. 2, for perfect temperature compensation at the upper surface of the sample platform, assuming that the housing C is at room ambient temperature, $$L_1 \times \alpha_1 \times \Delta T_1 = L_2 \times \alpha_2 \times \Delta T_2,$$

where, $\alpha_1$ is the coefficient of thermal expansion of the material used for the sample platform 12 and the support stem 14, and $\alpha_2$ is the coefficient of thermal expansion of the material used for the tubular wall member 18, and $L_1$ and $L_2$ are their respective lengths along the y direction, and $\Delta T_1$ and $\Delta T_2$ are the respective temperature gradients across the corresponding components.

Figure 5B:
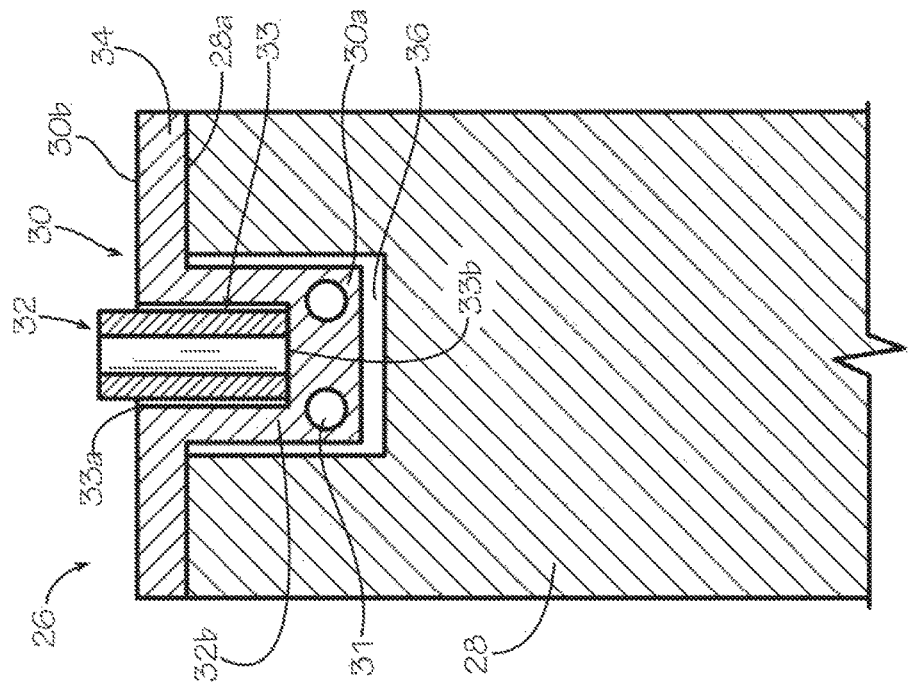
FIGS. 5A and 5B depict a tip holding stage according to an embodiment of the invention.
Figure 5A:
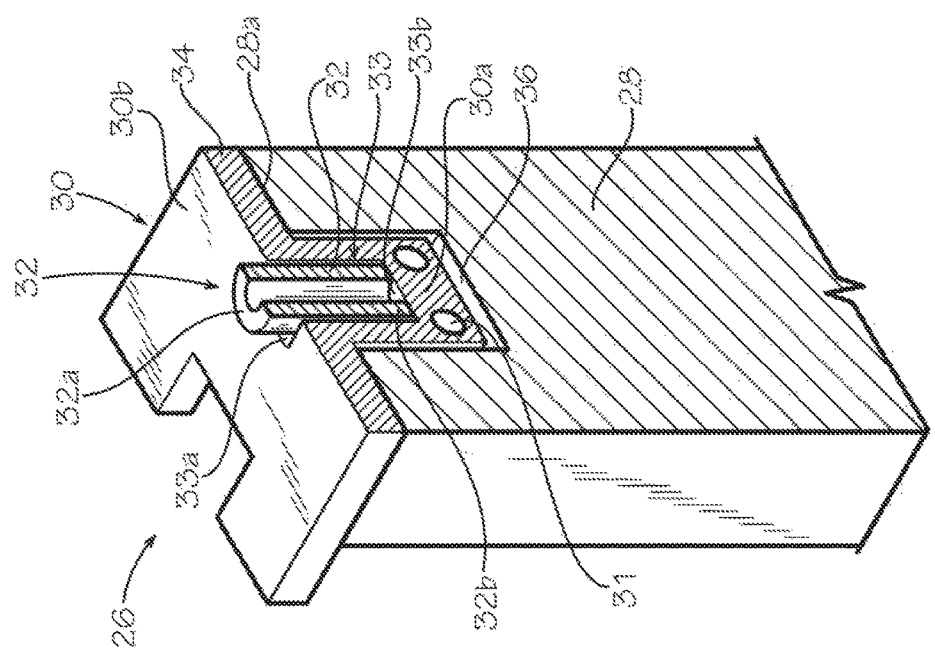

FIGS. 5A and 5B depict an embodiment of a nanoindentation tip holding stage 26 that includes a tip holder 32 for holding a nanoindentation tip (not shown). In a preferred embodiment, the tip holder 32 is formed from molybdenum. The tip holder 32 has a receiving portion 32a for receiving a nanoindentation tip and an attachment portion 32b. The tip holder 32 is disposed within a central bore 33 of a central portion 30a of a support structure 30, with the receiving portion 32a extending out from the bore opening 33a. In a preferred embodiment, the attachment portion 32b of the tip holder is fixedly attached to the bore end 33b at the bottom of the central bore 33. Thus, the tip holder 32 is firmly held and supported by the support structure 30, which in a preferred embodiment is formed from stainless steel. The receiving portion 32a of the tip holder 32 is free to move axially with respect to the bore opening 33a due to material expansion or contraction caused by temperature changes.

In some embodiments, a heat transfer element 31 is disposed within the central portion 30a of the support structure 30. The heat transfer element 31 may be an electric heater element for heating the tip holder 32, or a heat sink for cooling the tip holder 32. Multiple heat transfer elements 31 may be strategically placed to alter the transient response as desired.

The support structure 30 is held and supported by an extension shaft housing 28. The housing 28 has a central bore 36 that receives the central portion 30a of the support structure 30. An outer lip 34, which extends outwardly from the central portion 30a of the support structure 30, is fixedly attached to an outer surface 28a of the housing 28. In this configuration, the central portion 30a of the support structure 30 is free to move axially with respect to the central bore 36 as materials expand or contract due to temperature changes.

Thus, as the support structure 30 is heated (or cooled), the central portion 30a of the structure 30 moves downward (or upward), thereby compensating for expansion (or contraction) of the tip holder 32. This controls the steady state response to maintain the position of the receiving end of the tip holder 32.

In a preferred embodiment, the shaft housing 28 is formed from copper. It will be appreciated that various other combinations of materials may be used for the tip holder 32, support structure 30 and extension shaft 28.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention when interpreted in accordance with the breadth to which they are fairly, legally, and equitably entitled.

What is claimed is:

1. A sample holding stage for a measurement instrument, the sample holding stage comprising:
    a sample holder comprising:
        a sample platform having an upper surface upon which a sample may be placed and a lower surface disposed below the upper surface; and
        a tubular support stem having a stem upper portion that is rigidly affixed to the lower surface of the sample platform and a stem lower portion disposed below the stem upper portion;
    a support structure comprising:
        a base member that is rigidly affixed to the stem lower portion;

a tubular wall member having a wall lower portion that is rigidly affixed to the base member and a wall upper portion disposed above the wall lower portion; and a lip member affixed to the tubular wall member, the lip member having a central opening; and a housing comprising:

a central bore into which are received the base member and the tubular wall member of the support structure; and an upper ledge at least partially surrounding an upper portion of the central bore, wherein the lip member of the support structure is rigidly affixed to the upper ledge of the housing, wherein the tubular support stem of the sample holder is disposed inside the tubular wall member of the support structure, wherein at least a portion of the sample platform of the sample holder is disposed inside the central opening of the lip member of the support structure, wherein the sample platform can move axially with respect to the tubular wall member of the support structure due to thermal expansion or contraction, wherein the base member of the support structure can move axially with respect to the housing due to thermal expansion or contraction, and wherein the net axial displacement of the upper surface of the sample platform with respect to the upper ledge of the housing due to thermal expansion or contraction is no greater than 10 nanometers per degree change in temperature over a range of 25° C. to 1000° C.

2. The sample holding stage of claim 1 wherein the base member of the support structure has a central opening, and the tubular support stem of the sample holder is received within the central opening of the base member in a shrink fit configuration.

3. The sample holding stage of claim 2 wherein the tubular support stem and the central opening of the base member are cylindrical.

4. The sample holding stage of claim 1 further comprising a heat transfer element disposed within the sample platform for transferring heat into or removing heat from the sample platform.

5. The sample holding stage of claim 1 further comprising one or more sources or sinks of heat to statically and dynamically control temperature gradients and thereby expansions or contractions of components of the sample holding stage.

6. The sample holding stage of claim 1 wherein the lip member is clamped to an outer surface of the wall upper portion of the tubular wall member.

7. An indentation tip holding stage for a measurement instrument, the indentation tip holding stage comprising:

a housing comprising:

a housing outer surface; and a housing central bore extending into the housing from the housing outer surface;

a support structure comprising:

a central portion disposed at least partially inside the housing central bore;

a central portion outer surface disposed outside the housing central bore;

a support structure central bore extending into the central portion from the central portion outer surface, the support structure central bore having:

a central portion bore opening in the central portion outer surface; and a central portion bore end spaced apart from the bore opening; and a lip member extending outwardly from the central portion and rigidly affixed to the housing outer surface; and a tip holder disposed at least partially inside the support structure central bore, the lip holder comprising:

a receiving portion disposed adjacent the central portion bore opening, the receiving portion for receiving and holding an indentation tip; and an attachment portion disposed inside the support structure central bore and being rigidly affixed to the central portion or the support structure adjacent the central portion bore end;

wherein the central portion or the support structure can move axially within the housing central bore due to thermal expansion or contraction, and wherein the receiving portion of the lip holder can move axially within the support structure central bore due to thermal expansion or contraction.

8. The indentation lip holding stage of claim 7 wherein the lip holder is formed of molybdenum.

9. The indentation tip holding stage of claim 7 wherein the support structure is formed of stainless steel.

10. The indentation tip holding stage of claim 7 wherein the housing is formed of copper.

11. The indentation tip holding stage of claim 7 further comprising a heat transfer element disposed within the central portion of the support structure for transferring heat into or removing heat from the tip holder.

12. The indentation tip holding stage of claim 7 further comprising one or more sources or sinks of heat to statically and dynamically control the temperature gradients and thereby expansions or contractions.

13. The indentation tip holding stage or claim 7 wherein the net axial displacement of the receiving portion of the tip holder with respect to the central portion bore opening due to thermal expansion or contraction is no greater than 10 nanometers per degree change in temperature over a temperature range of 25° C. to 1000° C.

14. A sample holding stage for a measurement instrument, the sample holding stage comprising:

a sample holder formed of molybdenum comprising:

a sample platform having an upper surface upon which a sample may be placed and a lower surface disposed below the upper surface; and a tubular support stem having a stem upper portion that is rigidly affixed to the lower surface of the sample platform and a stem lower portion disposed below the stem upper portion;

a support structure comprising:

a base member that is rigidly affixed to the stem lower portion;

a tubular wall member having a wall lower portion that is rigidly affixed to the base member and a wall upper portion disposed above the wall lower portion; and a lip member affixed to the tubular wall member, the lip member having a central opening; and a housing comprising:

a central bore into which are received the base member and the tubular wall member of the support structure; and an upper ledge at least partially surrounding an upper portion of the central bore, wherein the lip member of the support structure is rigidly affixed to the upper ledge of the housing, wherein the tubular support stem of the sample holder is disposed inside the tubular wall member of the support structure, wherein at least a portion of the sample platform of the sample holder is disposed inside the central opening of the lip member of the support structure, wherein the sample platform can move axially with respect to the tubular wall member of the support structure due to thermal expansion or contraction, and wherein the base member of the support structure can move axially with respect to the housing due to thermal expansion or contraction.

15. A sample holding stage for a measurement instrument, the sample holding stage comprising:
    a sample holder comprising:
        a sample platform having an upper surface upon which a sample may be placed and a lower surface disposed below the upper surface; and
        a tubular support stem having a stem upper portion that is rigidly affixed to the lower surface of the sample platform and a stem lower portion disposed below the stem upper portion;
    a support structure formed of stainless steel comprising:
        a base member that is rigidly affixed to the stem lower portion;
        a tubular wall member having a wall lower portion that is rigidly affixed to the base member and a wall upper portion disposed above the wall lower portion; and
        a lip member affixed to the tubular wall member, the lip member having a central opening; and
    a housing comprising:
        a central bore into which are received the base member and the tubular wall member of the support structure; and
        an upper ledge at least partially surrounding an upper portion of the central bore, wherein the lip member of the support structure is rigidly affixed to the upper ledge of the housing,
    wherein the tubular support stem of the sample holder is disposed inside the tubular wall member of the support structure,
    wherein at least a portion of the sample platform of the sample holder is disposed inside the central opening of the lip member of the support structure,
    wherein the sample platform can move axially with respect to the tubular wall member of the support structure due to thermal expansion or contraction, and
    wherein the base member of the support structure can move axially with respect to the housing due to thermal expansion or contraction.

16. A sample holding stage for a measurement instrument, the sample holding stage comprising:
    a sample holder comprising:
        a sample platform having an upper surface upon which a sample may be placed and a lower surface disposed below the upper surface; and
        a tubular support stem having a stem upper portion that is rigidly affixed to the lower surface of the sample platform and a stem lower portion disposed below the stem upper portion;
    a support structure comprising:
        a base member that is rigidly affixed to the stem lower portion;
        a tubular wall member having a wall lower portion that is rigidly affixed to the base member and a wall upper portion disposed above the wall lower portion; and
        a lip member affixed to the tubular wall member, the lip member having a central opening; and
    a housing formed of copper comprising:
        a central bore into which are received the base member and the tubular wall member of the support structure; and
        an upper ledge at least partially surrounding an upper portion of the central bore, wherein the lip member of the support structure is rigidly affixed to the upper ledge of the housing,
    wherein the tubular support stem of the sample holder is disposed inside the tubular wall member of the support structure,
    wherein at least a portion of the sample platform of the sample holder is disposed inside the central opening of the lip member of the support structure,
    wherein the sample platform can move axially with respect to the tubular wall member of the support structure due to thermal expansion or contraction, and
    wherein the base member of the support structure can move axially with respect to the housing due to thermal expansion or contraction.

17. A sample holding stage for a measurement instrument, the sample holding stage comprising:
    a sample holder comprising:
        a sample platform that is cylindrical and has an upper surface upon which a sample may be placed and a lower surface disposed below the upper surface, the sample platform having a sample platform diameter that is larger than or equal to the sample diameter so as to accommodate the sample; and
        a tubular support stem having a stem upper portion that is rigidly affixed to the lower surface of the sample platform and a stem lower portion disposed below the stem upper portion;
    a support structure comprising:
        a base member that is rigidly affixed to the stem lower portion;
        a tubular wall member that is cylindrical and has a wall lower portion that is rigidly affixed to the base member and a wall upper portion disposed above the wall lower portion, the tubular wall member having an inner tubular wall diameter that is greater than the sample platform diameter, such that the sample platform can move axially with respect to the tubular wall member; and
        a lip member affixed to the tubular wall member, the lip member having a central opening that is cylindrical, and having a central opening inner diameter that is greater than the sample platform diameter, such that the sample platform can move axially with respect to the central opening of the lip member; and
    a housing comprising:
        a central bore into which are received the base member and the tubular wall member of the support structure, the central bore being cylindrical and having a central bore diameter that is greater than an outer tubular wall diameter of the tubular wall member, such that the tubular wall member can move axially with respect to the central bore of the housing; and
        an upper ledge at least partially surrounding an upper portion of the central bore, wherein the lip member of the support structure is rigidly affixed to the upper ledge of the housing,
    wherein the tubular support stem of the sample holder is disposed inside the tubular wall member of the support structure, wherein at least a portion of the sample platform of the sample holder is disposed inside the central opening of the lip member of the support structure,
wherein the sample platform can move axially with respect to the tubular wall member of the support structure due to thermal expansion or contraction, and
wherein the base member of the support structure can move axially with respect to the housing due to thermal expansion or contraction.

* * * * *